United States Patent [19]

Cinatl et al.

[11] Patent Number: 5,393,668
[45] Date of Patent: Feb. 28, 1995

[54] CULTIVATION OF MAMMALIAN CELLS IN A PROTEIN-FREE MEDIUM ON A POLYVINYLFORMAL AND/OR POLYVINYL BUTYRAL SURFACE

[75] Inventors: Jaroslaw Cinatl, Frankfurt am Main; Jindrich Cinatl, Obertshausen, both of Germany

[73] Assignee: Hans-Wilhelm Doerr, Germany

[21] Appl. No.: 943,238

[22] Filed: Sep. 10, 1992

[30] Foreign Application Priority Data

Sep. 11, 1991 [EP] European Pat. Off. ........... 91115336

[51] Int. Cl.⁶ ..................... C12N 5/00; C12N 11/08
[52] U.S. Cl. .................. 435/240.23; 435/180; 435/240.243
[58] Field of Search .......... 435/180, 240.23, 240.243

[56] References Cited

U.S. PATENT DOCUMENTS

| | | | |
|---|---|---|---|
| 4,419,243 | 12/1983 | Atkinson et al. | 210/618 |
| 4,498,985 | 2/1985 | Atkinson et al. | 210/151 |
| 4,545,909 | 10/1985 | Atkinson et al. | 210/618 |
| 4,582,600 | 4/1986 | Atkinson et al. | 210/151 |
| 5,081,036 | 1/1992 | Familletti | 435/286 |

OTHER PUBLICATIONS

Barnes et al., "Methods for Growth of Cultured Cells in Serum-Free Medium", *Analytical Biochemistry*, 102:255–270 (1980).

Cinatl et al., Protein-Free Cell Culture on Polyvinyl Formal Surface, *In Vitro Cell. Dev. Biol.: Anim.* Bd. 28A(3):147–148 (1992).

Black et al., Practical Reactor Systems for Yeast Cell Immobilization Using Biomass Support Particles, *Biotechnology and Bioengineering* XXVI: 134–141 (1984).

Cinatl et al., Quality Control Testing of Surfaces for Mammalian Cell Culture Using Cells Propagated in a Protein-free Medium, *Biologicals* 19:87–92 (1991).

Cinatl et al., A New Assay System For Quality Control Testing of a Chemically Defined Medium, *Journal of Tissue Culture Methods* 12(4):67–72 (1989).

Cinatl et al., A Novel Assay System For Quality Control Testing of Surfaces For Mammalian Cell Culture, *In Vitro Cell. Div. Biol.* 26:841–842 (1990).

Craig et al., Osteopontin, a Transformation-associated Cell Adhesion Phosphoprotein, Is Induced by 12-O-Tetradecanoylphorbol 13-Acetate in Mouse Epidermis, *J. Biol. Chem.* 264 (16):9682–9689 (1989).

Curtis et al., Substrate Hydroxylation and Cell Adhesion, *J. Cell Sci.* 86: 9–24 (1986).

Darfler, F. J., A Protein-Free Medium For The Growth of Hybridomas and Other Cells of The Immune System, *In Vitro Cell. Dev. Biol.* 26:769–778 (1990).

Familletti et al., Techniques For Mammalian Cell Immobilization, *Bio/Technology* 6:41–44 (1988).

Hata et al., L-Ascorbic Acid 2-Phosphate Stimulates Collagen Accumulation, Cell Proliferation, and Formation of a Three-Dimensional Tissuelike Substance by Skin . . . , *J. Cell. Physiol.* 138:8–16 (1989).

Kovář et al., Iron Compounds At High Concentrations Enable Hybridoma Growth In A Protein-Free Medium, *Biotechnology Letters* 9(4):259–264 (1987).

Kovář, J., Various Cell Lines Grow in Protein-Free Hybridoma Medium, *In Vitro Cellular & Developmental Biology* 25(5):395–396 (1989).

Nordby et al., Incorporation of Contrast Media in Cultured Cells, *Investigative Radiology* 24:703–710 (1989).

Roth et al., Influence of Two Glutamine-Containing Dipeptides on Growth of Mammalian Cells, *In Vitro Cellular & Developmental Biology* 24(7):696–698 (1988).

Schaeffer, W. I., Usage of Vertebrate, Invertebrate and Plant Cell, Tissue and Organ Culture Terminology, *In Vitro* 20(1):19–24 (1984).

*Primary Examiner*—David M. Naff
*Attorney, Agent, or Firm*—Sterne, Kessler, Goldstein & Fox

[57] ABSTRACT

Preferably, the cells are adherent cells such as Vero cells and the cells are cultivated as a continuous monolayer. The cells may be transfected with a gene construct which encodes a heterologous protein. Viruses of vaccines can be produced by culturing cells that have been infected with a virus.

7 Claims, 4 Drawing Sheets

Fig.1
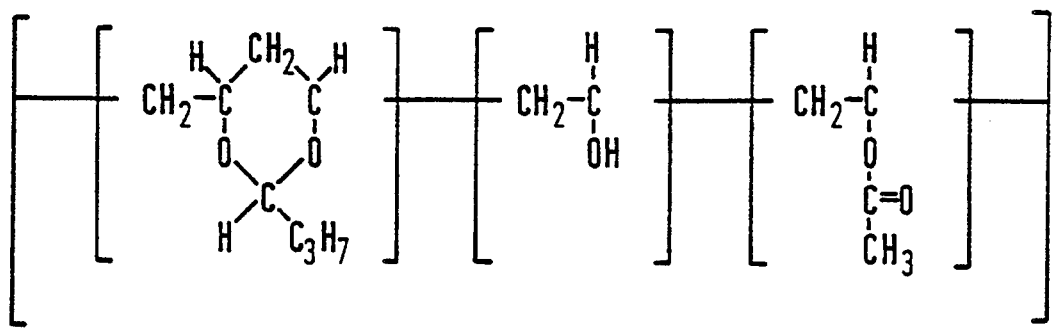
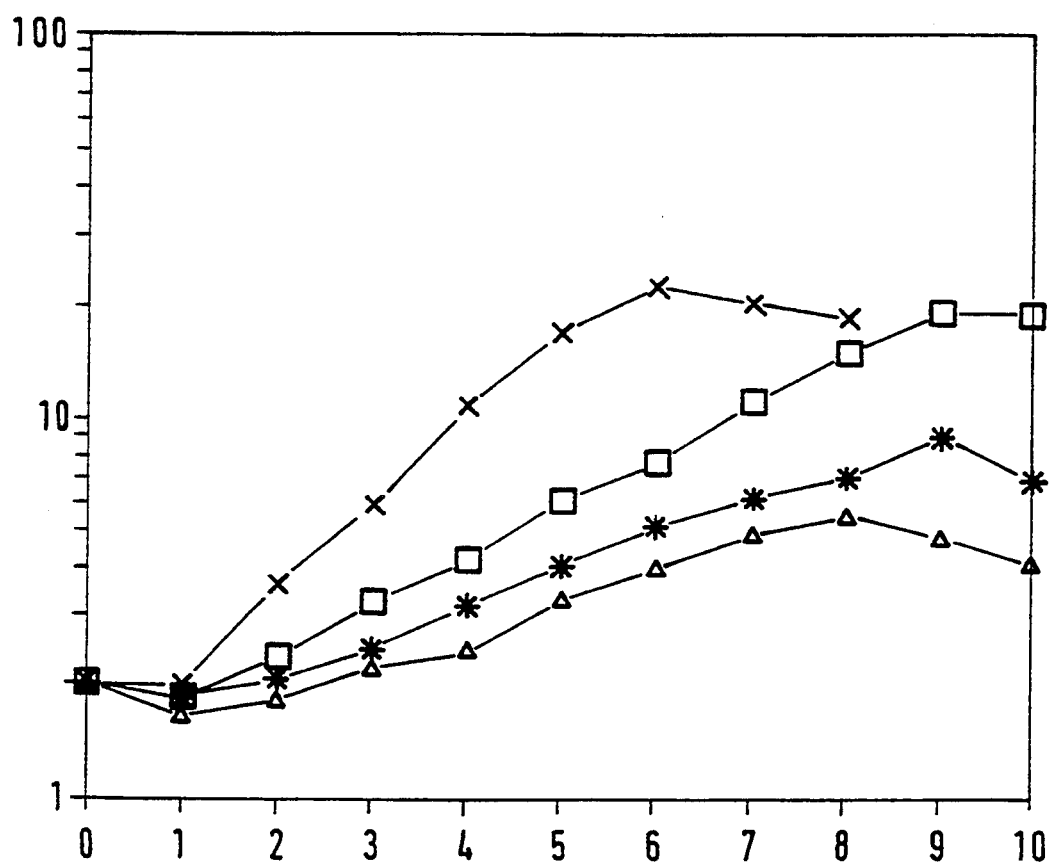
Fig.2

CULTIVATION OF MAMMALIAN CELLS IN A PROTEIN-FREE MEDIUM ON A POLYVINYLFORMAL AND/OR POLYVINYL BUTYRAL SURFACE

FIELD OF THE INVENTION

The invention concerns the cultivation of mammalian cells, especially the cultivation in serum-free medium. It is, for example, suitable for the cultivation of adherent cell lines including the production of virus-infected adherent cells.

BACKGROUND OF THE INVENTION

The cultivation of mammalian cells in a chemically defined protein-free medium has been known for more than 30 years (Evans, V. J., et al., Cancer Res. 16:77–86 (1956); Evans, V. J., et al., Am. J. Hyg. 70:297–302 (1959)); likewise, various cell lines, which have been established in protein-free medium (Evans, V. J., et al., Exp. Cell Res. 32:212–217 (1963); Cinatl and Vesely, Folio Biologica 13:61–67 (1967); Takoaka and Katsuta, Exp. Cell Res. 67:295–304 (1971); Sanford and Evans, J. Natl. Cancer Ins. 68:895–913 (1982); Okaba, T., et al., Proc. Natl. Acad. Sci. USA 81:453–455 (1984); Yamaguchi, N., et al., J. Natl. Cancer Inst. 75:29–35 (1985); Yamaguchi and Kawai, Cancer Res. 46:5353–5359, (1986); Kovar and Franek, Biotechnol. Lett. 9:259–264 (1987); Cinatl, J. Jr., et al., J. Biol. Stand. 16:249–257 (1988); Hill, M., et al., In Vitro Cell. Dev. Biol. 25:49–56 (1989); Rikimaru, K., et al., In Vitro Cell. Dev. Biol. 26:849–856 (1990)). Media which are available as commercial products and which enable cells to be grown in the absence of foreign proteins have only recently been developed (Fike, R., et al., In Vitro Cell. Dev. Biol. 26:54A (1990); Darfler, F. J., In Vitro Cell. Dev. Biol. 26:769–778 (1990)).

These known protein-free media are primarily suitable for growing continuous cell lines in a suspension, e.g., hybridomas (Kovar and Franek, Biotechnol. Lett. 9:259–264 (1987); Fike, R., et al., In Vitro Cell. Dev. Biol. 26:54A (1990); Darfler, F. J., In Vitro Cell. Dev. Biol. 26:769–778 (1990)), but on the other hand are frequently found to be unsuitable for promoting cell growth in monolayer cultures (Kovar, J., In Vitro Cell. Dev. Biol. 25:395–396 (1989)).

The significant influence of the properties of the culture surface on the growth of monolayer cultures in protein-free medium has been described (Sanford and Evans, J. Natl. Cancer Ins. 68:895–913 (1982); Price and Sanford, TCA Manual 2:379–382 (1976); Cinatl, J. Jr., et al., In Vitro Cell. Dev. Biol. 26:841–842 (1990)). Rappaport et al. found that the adhesion and growth of cells depended on a critical number of negative charges on the surface. They treated a glass flask by a special method with alkali which enabled the cultivation of various cell lines in a protein-free medium without a previous adaption phase (Rappaport, C., et al., Exp. Cell Res. 20:465–510 (1960)). This technique of preparing the culture surface is, however, complicated and restricted to glass. Besides, different artificial surfaces from various suppliers were tested in assays using cells in serum-containing media and other protein additives. The results of these investigations showed that for the growth of cells in protein-free media, a different quality of the culture-surface is required as for the growth of cells in serum-containing media.

It has been known for years that the properties of the surface of glass or plastics has a significant influence on the growth of monolayer cells in protein-free medium [Sanford and Evans, J. Natl. Cancer Ins. 68:895–913 (1982); Price and Sanford, TCA Manual 2:379–382 (1976); Cinatl, J. Jr., et al., In Vitro Cell. Dev. Biol. 26:841–842 (1990)). It can be seen from the literature that not only the composition but also the properties of the culture surface must be optimized in order to achieve a satisfactory growth of cells in such a medium.

Polyvinylformal (PVF) was used for the first time as culture surface by Barski and Maurin for various cell types in media containing serum, embryonal extract and Tyrodes' salt solution. Other authors used PVF for some time for growing various cell lines in media containing protein additives (Furusawa, K., et al., Kenkyu Hokoku-Sen'i Kobunshi Zairyo Kenkyosho 124:17–21 (1980); Craig, A. M., et al., J. Biol. Chem. 264:9682–9689 (1989); Nordby, A., et al., Invest. Radiol. 24:703–710 (1989)).

Commercial disposable plastics articles, including polystyrene (PS), possess mainly negative surface charges. Maroudas has established that a negative charge density of $2-10 \times 10^{14}$ per $cm^2$ is optimal for cell proliferation, e.g., PS-TC (polystyrene-tissue culture grade) has a negative charge density of $4-7 \times 10^{14}$ per $cm^2$. On the other hand, PVF has a negative charge density of only $0.4-0.8 \times 10^{14}$ per $cm^2$.

SUMMARY OF THE INVENTION

The invention relates to an improved process for the cultivation of adherent cells in protein-free medium, the improvement comprising employing a culture surface comprising polyvinylformal and/or polyvinylbutyral.

The invention also relates to an improved bioreactor for cultivating cells in protein-free medium, characterized in that a culture surface is employed which comprises PVF and/or PVB in said reactor.

DESCRIPTION OF THE FIGURES

FIG. 1 shows the stylized formulae of PVF with hydroxyl groups, acetate groups and formal-groups which are distributed randomly along the molecule. Formvar compound of PVF contains 5–5.6% polyvinyl alcohol, 9.5–13% polyvinyl acetate and 82% polyvinyl formal.

FIG. 2 shows the growth curve of Vero cells in MEM with 10% FBS added (-x-) and of Vero cells in the protein-free medium on PS-TC- (-△-), on poly-D-lysine (-*-) and on PVF-surface (-□-). The x axis represents the number of days in culture, and the y axis the population doubling level.

DESCRIPTION OF THE PREFERRED EMBODIMENTS

Figure 3A:
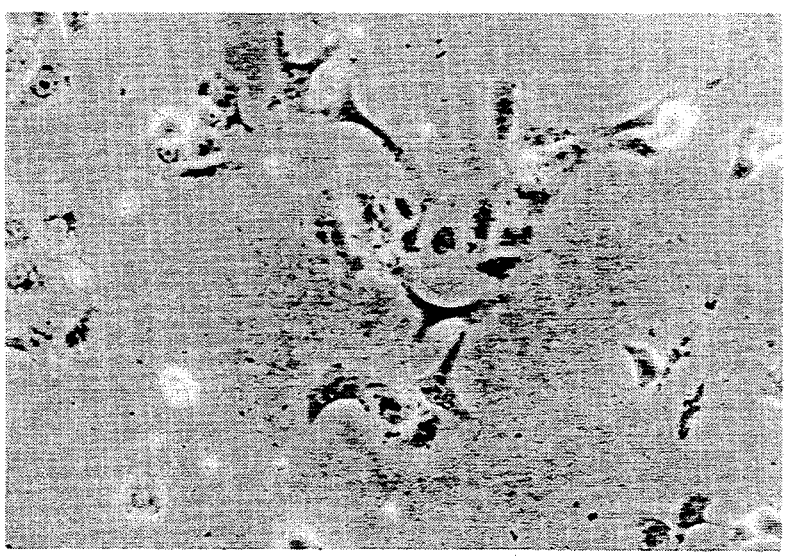
FIG. 3 shows the morphological appearance by contrast microscope of Vero cells in protein-free medium on PS-TC surfaces (A), poly-D-lysine surface (B) and PVF-surface (C), 9 days after the inoculation phase.

The object of the invention is to provide a new culture surface for the cultivation of various cell lines in a protein-free medium, preferably as a continuous monolayer. It has been surprisingly found that the use of PVF and/or PVB as cell substrate fulfills this objective.

In one aspect, the invention therefore provides a process for the cultivation of adherent cells in protein-free medium, characterized in that a culture surface composed of polyvinylformal and/or polyvinylbutyral is used. Such adherent cells are also known as anchorage-dependent cells.

Polyvinylformal (PVF) and polyvinylbutyral are known polymers belonging to the "Polyvinylacetals" which are formed by reaction of aldehyde (formaldehyde or butyraldehyde) and polyvinylalcohol. As is well known, by using suitable amounts of starting monomers, it is possible to obtain PVF and PVB with different, predetermined contents of, e.g., hydroxyl groups, e.g., the commercially available products Butvar® B-98 (Monsanto Company, Texas) contains 20% hydroxyl as polyvinyl alcohol and Butvar® B-76 13% hydroxyl calculated on the same basis; various Formvar® resins such as, e.g., Formvar® 5/95E and 15/95E contain only 6.5 % hydroxy as polyvinyl alcohol. Butvar® is thus more hydrophilic than Formvar®. PVF and PVB can be used alone or as a mixture.

Preferably, the cells are cultivated as a continuous monolayer.

The process of the invention is especially suitable for the cultivation of Vero-cells. Other adherent cells which can be used in the practice of the invention include, but are not limited to, chinese hamster ovary (CHO) cells, human fibroblasts, human tumor cells of mesenchymal or epithelial origin, COS cells, BHK cells, hepatoma cells, human diploid fibroblasts, virus transformed cells, avian cells, amphibian cells and insect cells. Most eukaryotic cells provide post translational modification to recombinant protein molecules which provide for correct folding and glycosylation of appropriate sites.

In a preferred embodiment, the adherent cells utilized in the practice of the invention have been transfected with a gene construct which encodes a heterologous protein. A particular gene for expression by the eukaryotic cell line may be obtained by any of the means known to those skilled in the art. See Maniatis, T. et al., Molecular Cloning-A Laboratory Manual. Cold Spring Harbor Laboratory, Cold Spring Harbor, New York (1982). Genomic or cDNA sequences may be used in the practice of the invention. Genomic sequences are expressed efficiently in eukaryotic cells, since they contain native promoter structures.

The joining of various DNA fragments is performed in accordance with conventional techniques, employing blunt-ended or staggered-ended termini for ligation, restriction enzyme digestion to provide appropriate termini, filling in of cohesive ends as appropriate, alkali and phosphatase treatment to avoid undesirable joining, and ligation with appropriate ligases. The genetic construct may optionally encode a leader sequence to allow efficient expression of the recombinant protein. The cDNA may be cloned, and the resulting clone screened, for example, by use of a complementary probe or by assay for expressed recombinant protein using an antibody.

To express the recombinant protein, transcriptional and translational signals recognized by an appropriate host element are necessary. In general, vectors containing replicon and control sequences derived from species compatible with a host cell are used in connection with the host. The vector ordinarily carries a replicon site, as well as specific genes which are capable of providing phenotypic selection in transformed cells. The expression of the recombinant protein can also be placed under control with other regulatory sequences which may be homologous to the cell line in its untransformed state.

For eukaryotic hosts, several possible vector systems are available for expression. One class of vectors utilize DNA elements which are derived from animal viruses such as bovine papilloma virus, polyoma virus, adenovirus, vaccinia virus, baculovirus, retroviruses (RSV, MMTV or MOMLV), or SV40 virus. Cells which have stably integrated the DNA into their chromosomes may be selected by introducing one or more markers which allow selection of transfected host cells. The marker may provide for prototropy to an auxotrophic host, biocide resistance, e.g., antibiotics, or heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements includes those described by Okayama, H., Mol. Cel. Biol., 3:280 (1983) and others.

Once the vector or DNA sequence containing the constructs has been prepared for expression, the DNA constructs may be introduced to the eukaryotic cell line. Various techniques may be employed, such as protoplast fusion, calcium phosphate precipitation, electroporation or other conventional techniques. The transfected cells may then be screened for the appropriate activity.

Suitable serum-free media are, for example, a 1:1 modified DMEM/F12-Medium (containing additionally trace elements, Vitamin-C phosphate and glutamine dipeptide), Ham's F-10, Ham's 12, $\alpha$-MEM or DEM/F12 without trace elements and Vitamin-C.

The above-mentioned modified mixture of DEM/F12 is preferred.

A further preferred medium composition which can, e.g., improve the growth kinetics of the Vero cells is a mixture of the two following media:

1. Hybridmax (Sigma) and
2. SRE-199 (Sigma)

in the ratio 1:1 with 800$\mu$g/mi $CaCl_2$.

It is straightforward for the skilled artisan to test available media analogously to the examples herein, in order to identify suitable media.

Preferably, the cells are incubated with a starting cell density of at least $2.0 \times 10^4$ cells/cm$^2$.

A further aspect of the present invention for cultivation of cells in a serum-free medium is the use of a cultivation reactor which contains a culture surface composed of PVF and/or PVB.

Various filling bodies such as, e.g., saddels, steel spirals, glass or ceramic beads coated with PVF and/or PVB, can be used to provide the culture surface. Where stainless steel is employed, it may be in the form of sheets, small particles, compressed wire, strands, woven mesh, or sponge-like material. See, for example, Black, G. M., et al., *Biotechnology and Bioengineering* 26:134-141 (1984) and Atkinson et al., U.S. Pat. Nos. 4,545,909 (1985); 4,498,985 (1985); 4,419,243 (1983) and 4,582,600 (1986); Fukuda, H., et al., Third European Congress on Biotechnology, Munich, W. Germany, 1:547-552 (1984); the disclosures of which are fully incorporated by reference herein. See also, Familletti, P. C. et al., *Bio/Technology* 6:41-44 (1988), the disclosure of which is fully incorporated by reference herein.

Although the culture vessel or filling bodies may consist entirely of PVF and PVB, they will usually consist of a base structure of metal, glass or plastics material with a thin overlayer of PVF and/or PVB. Preferably, such a thin overlayer is produced by bringing the base structure into contact with a solution of PVF and/or PVB and evaporating, or allowing the solvent to evaporate.

The process of the invention is suitable for preparing biological substances by cultivating cells which produce the substance as an endogenous protein or as a recombinant protein. By the term "biological substance" is intended any natural substance or recombinant protein which can be produced by expression of a heterologous gene in a transfected anchorage-dependent eukaryotic cell line. To this end, e.g., a mammalian cell which has been transformed by a gene coding for a foreign protein can be cultivated on the PVF and/or PVB culture surface in a protein-free medium and the protein isolated and purified in known manner after the end of the cultivation. Examples of such biological substances are, but are not limited to, e.g., t-PA, EPO, hGH, ICAM-1, human lung surfactant proteins such as, e.g., SP-B, SP-C, metabolites, hormones, interleukins or inteferons.

The process of the invention is suitable for the production of viruses or vaccines, whereby cells (especially Vero cells) infected with virus (e.g., Poliovirus, Adenovirus, BVD), are cultivated on the PVF and/or PVB culture surface in protein-free medium, and after cultivation the virus isolated and worked up by known methods.

The following examples are illustrative, but not limiting, of the methods and apparatuses of the present invention. Other suitable modifications and adaptations of the variety of the conditions and parameters normally encountered in the field of cell culture technology, which are obvious to those of skill in the art, are within the scope of this invention.

EXAMPLE 1

A polyvinylformal solution was obtained by dissolving pulverized polyvinylformal (PVF, FIG.1) (Formvar ®; Monsanto Company, Texas, USA) in acetic acid in various concentrations of 1 to 20 mg/ml. The resulting solutions were applied in amounts of 5 ml or 3 ml respectively to the culture surfaces of 25 cm$^2$ PS-TC culture flasks (Falcon, Heidelberg, FRG, and Greiner, Nürtingen, FRG) and dishes (Greiner, Nürtingen, FRG); after 2 minutes the solution was decanted. The flasks were kept for 24 hours in a laminar flowhood, in order to evaporate the residual acetic acid. Thereafter, the flasks were washed with double distilled water and used either immediately or up to three months thereafter, for cell cultivation.

The negative charge density of the surface of the vessels was measured by cationic dye (crystal violet) binding (described by Maroudas; Kovar and Franek, *Biotechnol. Lett.* 9:259-264(1987); Maroudas, N. G., *J. Cell. Physiol.* 90:511-520 (1976)).

It was assumed that the number of molecules bound to the surface was identical to the absolute number of fixed negative charges.

The cell lines used were murine NCTC Clone 929L and Swiss 3TC, Syrian hamster BHK-21 Clone 13, Chinese hamster CHO-K1, porcine PK-15, canine MDCK, monkey Vero and LLC MK2, human A431 and HeLa cell lines of the American Type Culture Collection.

Stock cultures of these cells, with the exception of CHO-cells, were multiplied in MEM containing 5-10% fetal bovine serum containing 10% FBS.

All cells were cultured in culture flasks with a culture surface of 75 cm$^2$ in a $CO_2$ incubator (37° C., 5% $CO_2$). The cells were routinely monitored, to identify any mycoplasma, by means of Hoechst 33258 DNA staining method. All stainings proved negative.

The protein-free medium was a modified 1:1 mixture of DMEM-F12 containing 15 mM HEPES and 1.2 g/l sodium bicarbonate (Table 1). The use of glycyl-L glutamine instead of L-glutamine results in a higher concentration of glycine in the medium. This, however, has no influence on the proliferation of the various cells.

In order to start the cell cultures in protein-free conditions, the confluent culture was washed three times with PBS and freed from the culture surface with a 2:1 mixture of collagenase H 0.25% and dispase 0.25% in PBS. The released cells were washed three times with PBS and inoculated in protein-free medium and finally incubated in a $CO_2$ incubator (37° C., 5% $CO_2$).

In order to measure cell growth and adhesion, the cells were washed three times with PBS and, at various time intervals from the inoculation, released from the culture surface using Trypsin 0.1% in PBS, and then the living cells counted using a Hemocytometer.

The viability of the cells was determined using the dye-exclusion method after staining with 0.5% trypan blue solution.

The saturation density of the cell population was estimated as the maximal cell number which can be attained under specific culture conditions (Schaeffer, W. I., *In Vitro Cell. Dev. Biol.* 20:19-24 (1984)). The number of population doubling levels (PDL) were calculated from the original number of cells seeded (Ni) and the number of harvested cells (Nf) using the formula PDL=3.32 log (Nf/Ni) (Schaeffer, W. I., *In Vitro Cell. Dev. Biol.* 20:19-24 (1984)).

EXAMPLE 1

Poliovirus types 1 and 3, clinical isolates and Adenovirus types 2 and 5 were isolated from adenoid tissue. The identities of the viruses were determined by serum-neutralization tests using the standardized polioviruses of the types 1 to 3 and adenovirus type 2 and 5 antisera. All viruses were propagated and titrated in Vero cells maintained in MEM, supplemented with 3% FBS.

In order to avoid contamination of the protein-free medium with serum protein from the above virus stocks, only intracellular viruses from the infected cultures were used in the following investigation.

The infected cells were scraped from the culture surfaces, washed three times with PBS, and each time suspended in fresh protein-free medium. The cells were thereafter disrupted by sonication, centrifuged (1200×g) and the virus-containing supernatant frozen at −70° C.

Confluent cultures of Vero cells were cultured growing on PVF-culture surfaces in protein-free medium in 35 mm culture dishes and after washing 5 times with PBS were infected with 0.2 ml of virus suspension containing poliovirus at MOI 0.01 PFU/cell and adenovirus at MOI 0.5 PFU/cell. After one hour at 37° C, the inoculum was removed, the cells washed with PBS and 2 ml of protein-free DMEM/F12 virus titration by plaque assay carried out. For this assay, the supernatant of the infected cultures was diluted (in two stages).

In the plaque assay, the confluent layers of Vero cells grown in serum supplemented medium were washed twice with PBS and 0.2 ml of each dilution added. After 1 hour incubation at 37° C., the inoculi were removed, the cells washed with PBS and 2 ml of 1% carboxymethyl cellulose in MEM with 2% FBS added. Three dishes were used for each virus dilution. After 4 days (poliovirus) and 7 days (adenovirus) visible plaques were counted after staining with 0.2% crystal violet.

Results

In Table 2, the effect of PVF surfaces on the growth of ten continuous cell lines in protein-free DMEM/F12 are compared with the effect of PS-TC or poly-D-lysine.

All cells were seeded at a density of $2 \times 10^4$ cells/cm$^2$. The results correspond to the saturation density of the cells in the various time intervals between 5 and 9 days.

3T6 was the only cell line, which showed minimal attachment to PVF and essentially no spreading, whilst 3T6 cells on PS-TC or poly-D-lysine showed proliferation beginning immediately following adhesion.

Figure 3B:
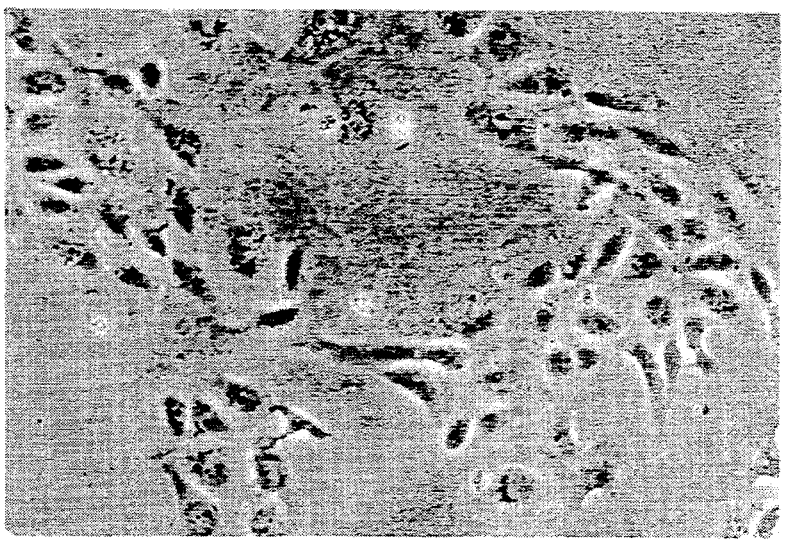
Figure 3C:
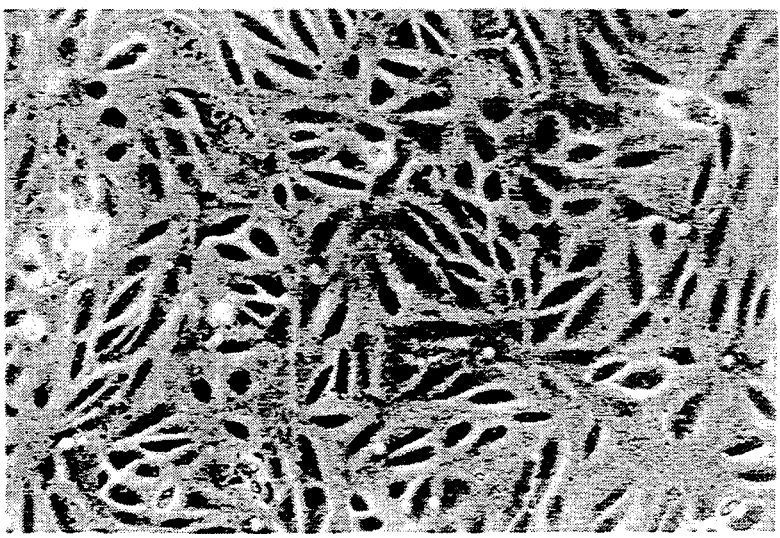

Six cell lines including the NCTC clone 929L, BHK, CHO-K1, PK 15, A431 and HeLa showed the same proliferation on PVF as on commercial PS flasks. In most cases, cell growth could be increased by pre-coating PS-TC with poly-D-lysine; a confluence of more than 75% could not, however, be achieved. Two cell lines including MDCK and LLC-MK2 proliferated significantly better on PVF as on PS-TC. The proliferation of MDCK on PVF was slightly greater than that of the cells on the Poly-D-lysine culture surface. These cells, however, neither could achieve a confluent layer nor a continuous growth. In contrast the Vero cells grew better on PVF as on PS-TC or Poly-D-lysine coated surfaces. On day 9 after seeding the cells had reached confluency (FIG. 2 and 3). The population-doubling time of the Vero cells on PVF in protein-free medium was reached after 48 hours, in DMEM-F12, 10% FBS containing medium after 28 hours. The saturation density of the cells when using serum containing medium was approximately only 17% higher than that when using protein-free medium on PVF (FIG.2).

In Table 3 the effect of the various surfaces on adhesion of Vero cells in protein-free medium is shown. The cells attached and spread more rapidly on Poly-D-lysine and PVF than on PS-TC surface. This was most obvious 30 minutes after seeding. The number of cells attached to the PS-B surface was similar to that of the cells on PS-TC, and also some initial proliferation was observed.

The results in Table 4 show that proliferation of Vero cells on PVF in the protein-free medium was strongly dependent on the number of seeded cells, such that only when the starting Vero cell density was greater than $0.2 \times 10^4$ cells/cm$^2$ did an increase in cell number occur. However, some initial proliferations of Vero cells occurred on PS and Poly-D-lysine only when cells were seeded at initial density of $2 \times 10^4$ cells/cm$^2$ and $1 \times 10^4$ cells/cm$^2$ respectively.

Table 5 shows the growth of Veto cells in protein-free DMEM-F12 on PVF prepared from Formvar solutions at various concentrations. The saturation density did not differ markedly on PVF surfaces prepared from Formvar at concentrations ranging from 0.5% to 2%. In contrast, the saturation density of the cells on PVF prepared from 0.1% was significantly decreased.

Table 6 shows that PVF surfaces could be used in the course of three months after their preparation without any decrease in growth rate of the Vero cells in culture free medium.

The measurement of negative surface charge density showed significant differences between PS-TC and PVF surfaces. On the other hand, no significant differences between PVF and PS-B were observed. The range of negative surface charge density was $4$–$7 \times 10^{14}$ per cm$^2$ for PS-TC, $0.3$–$0.7 \times 10^{14}$ per cm$^2$ for PS-B and $0.4$–$0.8 \times 10^{14}$ per cm$^2$ for PVF.

Figure 4:
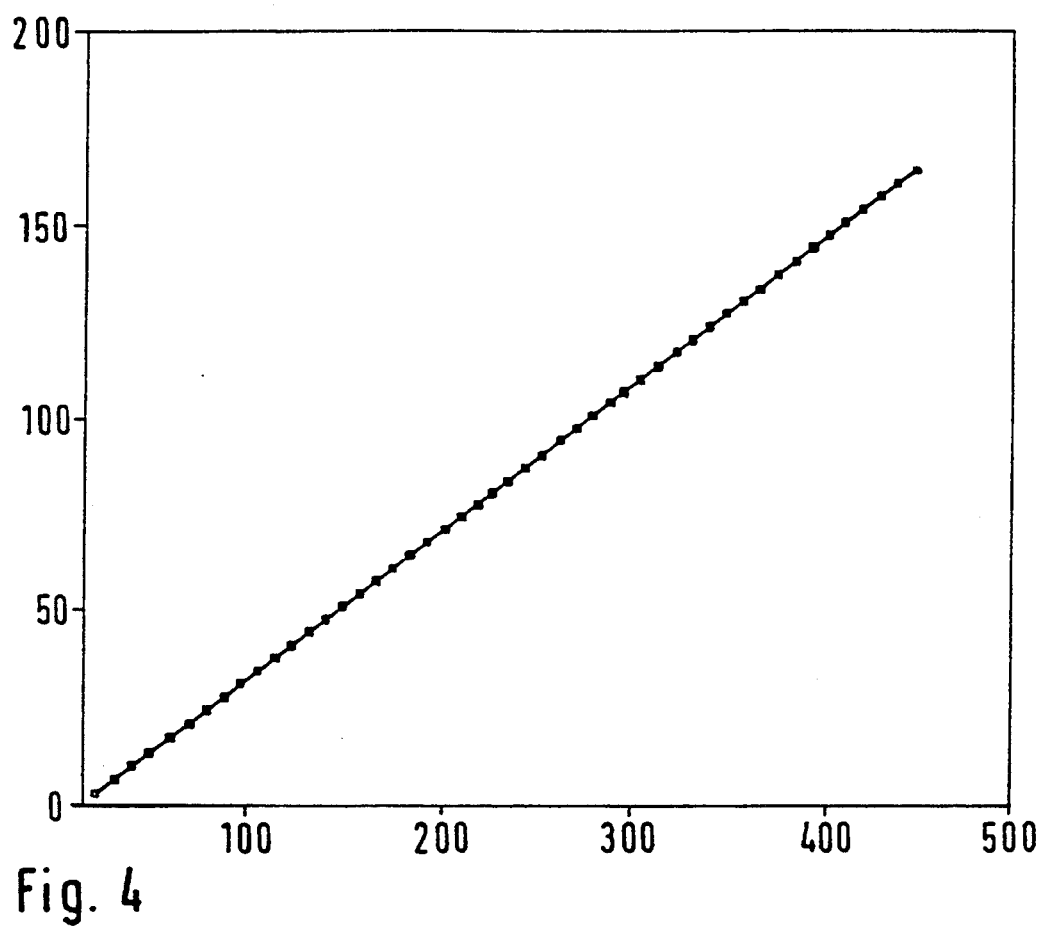
FIG. 4 shows the long-term cultivation of Vero cells in protein-free medium on PVF surface layer. The cells were subcultured in intervals of 9 days using a collagenase dispase solution and seeded at a density of $2.5 \times 10^4$ cells per $cm^2$. The x axis represents the number of days in culture, and the y axis the population doubling level.
Figure 5:
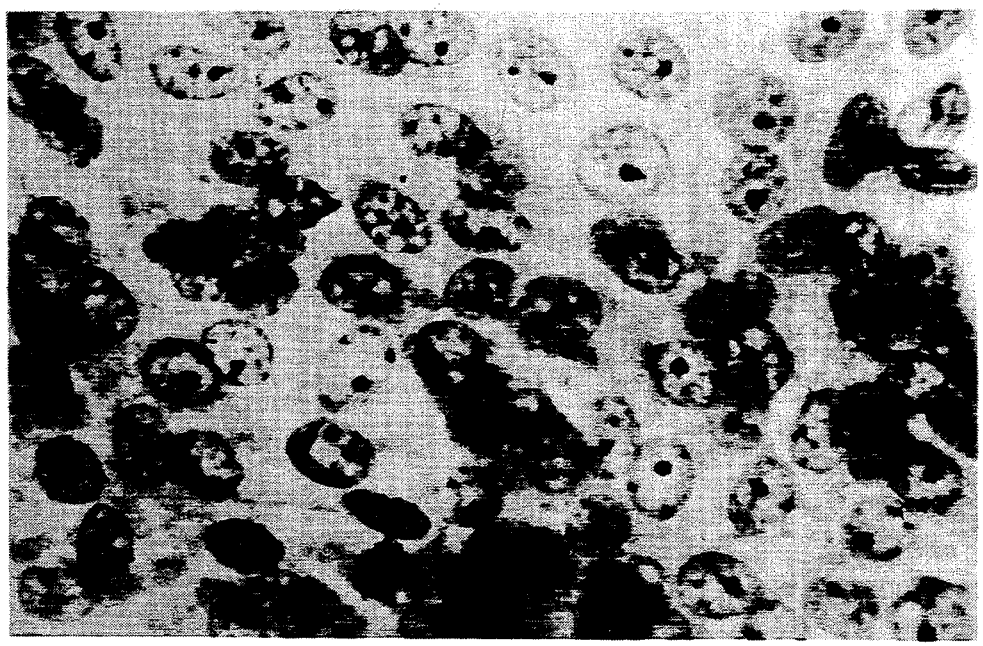
FIG. 5 shows the morphological appearance of Vero cells after 40 passages in protein-free medium on PVF surfaces. The cells were stained with May-Grünwald-Giemsa, a well-known commercially available stain.

Vero cells could be sub-cultivated in the protein-free medium without any significant decrease of growth rate in successive passages and as much as fifty sub-cultures. 164 Population doublings have been achieved (FIG. 4). The morphological appearance of Veto cells established in protein-free medium did not differ from that of the cells grown in serum supplemented medium (FIG. 5). In addition FIG. 5 shows that no background staining occurred after staining with May-Grünwald-Giemsa.

The PVF-coating in the above example possesses optical properties which are similar to those of the PS-culture flask. In addition, no background colouring of PVF is noticeable after colouring with May-Grünwald-Giemsa. Several PVF compositions have been tested, having different proportions of hydroxy and acetate, but which showed similar effects in the spreading of Vero cells. By virtue of its properties and low cost PVF is especially suitable for use as culture surface for Vero cells and also LLC-MK2 and MDCK cells, whose spreading in protein-free medium on PVF is likewise increased. As Vero cells are often used in the production of virus vaccines and other biologically active substances, PVF coated microcarriers for example can be used in the production of biological substances.

In the above examples relatively simple protein-free media have been used. It is to be expected that improved protein-free media would lead to an increase in the growth rate of cells on PVF. It must be taken into account that the successful growth of the various cells in protein-free medium is dependent on various factors including purity of water, chemical purity of the glass and plastics and the quality of chemicals (Sanford and Evans, *J. Natl. Cancer Ins.* 68:895–913 (1982); Price and Sanford, *TCA Manual* 2:279–382 (1976); Cinatl, J. Jr. et al., *In Vitro Cell. Dev. Biol.* 26:841–842 (1990); and Cinatl, J. Jr., et al., *J. Tissue Cult. Methods* 12:67–72 (1989)). The protein-free medium has been supplemented herein with glycine-L-glutamine instead of L-glutamine (Roth, E., et al., *In Vitro Cell. Dev. Biol.* 24:696–698 (1988)) and with L-ascorbic-2-phosphate (Hata and Senoo, *J. Cell. Physiol.* 138:8–16 (1989)). It is to be supposed that the use of this stable substance increases the proliferation of the various cells in the protein-free medium.

From the foregoing description, one skilled in the art can easily ascertain the essential characteristics of this invention, and without departing from the spirit and scope thereof, can make various changes and modifications of the invention to adapt it to various usages and conditions without undue experimentation.

TABLE 1

Substances added to protein-free DMEM-F12

| Substance | Concentration in medium mg/l | Source* |
|---|---|---|
| $CoCl_2.H_2O$ | 0.0002 | S |
| $CuSO_4.5H_2O$ | 0.00025 | S |
| $MnSO_47H_2O$ | 0.000024 | SE |
| $Na_2SeO_3$ | 0.0005 | S |
| $Na_2SiO_3.9H_2O$ | 0.0065 | I |
| $NH_4VO_3$ | 0.00006 | SE |
| $NiCl_2.6H_2O$ | 0.00012 | SE |
| $(NH_4)_6Mo_7O_{24}.H_2O$ | 0.00012 | SE |
| $SnCl_2.2H_2O$ | 0.00001 | S |
| L-Ascorbic Acid 2-phosphate-magnesium salt | 28.95 | W |
| Glycyl-L-glutamine | 800.00 | PK |

*S = Sigma;
SE = Serva (Heidelberg, FRG);
I = ICN Biochemicals (Mechenheim, FRG);
W = Wako Pure Chemical Industrie, Ltd. (Osaka, Japan);
PK = Pfrimmer - Kabi (Erlangen, FRG).

TABLE 2

Effect of different surfaces on saturation density of ten mammalian cell lines in the protein-free medium

| Cell line | Origin Tissue | Species | PS-TC | Poly-D-Lysine | PVF |
|---|---|---|---|---|---|
| NTCT clone 929 | subcutaneous and adipose | mouse | 4.6 ± 0.18(+) | 7.3 ± 9.46(++) | 4.2 ± 0.27(+) |
| 3T6 | embryo | mouse | 8.1 ± 0.45(++) | 9.3 ± 0.52(+++) | 2.5 ± 0.19(+) |
| BHK | kidney | hamster | 4.5 ± 0.31(+) | 5.1 ± 0.39(+) | 4.9 ± 0.29(+) |
| CHO-K1 | ovary | chinese hamster | 5.1 ± 0.38(+) | 7.2 ± 0.38(++) | 5.7 ± 0.32(+) |
| PK 15 | kidney | pig | 6.9 ± 0.49(++) | 7.9 ± 0.43(++) | 7.4 ± 0.45(++) |
| MDCK | kidney | dog | 4.9 ± 0.31(+) | 8.3 ± 0.48(++) | 10.4 ± 1.62(++) |
| Vero | kidney | monkey | 5.6 ± 0.29(+) | 8.1 ± 0.41(++) | 19.2 ± 2.10(++++) |
| LLC-MK2 | kidney | monkey | 5.2 ± 0.31(+) | 9.8 ± 0.51(+++) | 8.7 ± 0.51(++) |
| A431 | epidermoid carcinoma | human | 5.9 ± 0.49(+) | 10.1 ± 1.70(+++) | 6.3 ± 0.51(+) |
| HeLa | cervix carcinoma | human | 6.6 ± 0.43(++) | 8.1 ± 0.43(++) | 5.9 ± 0.39(+) |

PVF surface was prepared from 1% formvar solution. Values represent means from four dishes ±SEM. Cell achieved maximal 25% confluency (+), 50% confluency (++), 75% confluency (+++) or confluent cell layer (++++).

TABLE 3

Effect of different surfaces on adhesion of vero cells in protein-free medium

| Time after seeding (hours) | Cell number/cm² × 10⁻⁴ | | | |
|---|---|---|---|---|
| | PS-B | PS-TC | Poly-D-Lysine | PVF |
| 30 | 1.31 ± 0.21 | 1.49 ± 0.23 | 1.81 ± 0.25 | 1.74 ± 0.19 |
| 60 | 1.56 ± 0.19 | 1.61 ± 0.21 | 1.78 ± 0.21 | 1.86 ± 0.23 |
| 90 | 1.61 ± 0.22 | 1.68 ± 0.26 | 1.83 ± 0.18 | 1.85 ± 0.25 |

PVF surface was prepared from 1% formvar solution. Values means from four dishes ±SEM.

TABLE 4

Effect of initial cell density on the proliferation of Vero cells on PVF surface in protein-free medium

| Initial cell density per cm² × 10⁻⁴ | Final cell density per cm² × 10⁻⁴ | | |
|---|---|---|---|
| | PS-TC | Poly-D-Lysine | PVF |
| 2 | 5.5 ± 0.29 | 8.9 ± 0.45 | 18.9 ± 2.9 |
| 1 | 2.2 ± 0.21 | 4.6 ± 0.31 | 14.2 ± 2.1 |
| 0.5 | 0 | 0 | 6.9 ± 0.4 |
| 0.2 | 0 | 0 | 3.8 ± 0.3 |
| 0.1 | 0 | 0 | 0 |

PVF surface was prepared from 1% formvar solution. Values are means from four dishes ±SEM.

TABLE 5

Effect of PVF surface prepared from formvar solutions at various concentrations on saturation density of Vero cells in protein-free medium

| Concentration of PVF in % | cell number per cm² × 10⁻⁴ |
|---|---|
| 0.10 | 12.5 ± 2.5 |
| 0.50 | 18.6 ± 3.1 |
| 1.00 | 18.3 ± 2.8 |
| 2.00 | 18.9 ± 2.4 |

Values represent means from four dishes. The cells were counted 9 days after seeding.

TABLE 6

Effect of PVF surface stored for various time intervals on saturation density of Vero cells in protein-free medium

| Days after preparation | Number of cells/ cm² × 10⁻⁴ |
|---|---|
| 1 | 19.1 ± 2.3 |
| 30 | 18.1 ± 2.1 |
| 90 | 18.7 ± 2.9 |

PVF surface was prepared from 1% formvar solution. Values represent means from four dishes ± SEM. The cells were counted 9 days after seeding.

We claim:

1. In a process for the cultivation and proliferation of Vero cells in a protein-free medium, wherein said cells are in contact with and cultured on a culture surface, the improvement comprising culturing said cells on a polyvinylformal and/or polyvinylbutyral culture surface.

2. The process of claim 1, wherein polyvinylformal is the culture surface.

3. The process of claim 1 or 2, wherein the Vero cells are cultivated as continuous monolayers.

4. The process of claim 1 or 2, wherein the Vero cells are infected with a virus.

5. The process of claim 1 or 2, wherein the Vero cells are capable of producing a desired biological substance as a natural product.

6. The process of claim 1 or 2, wherein the Vero cells are capable of producing a desired biological substance as a recombinant product.

7. The process of claim 1, wherein the Vero cells are seeded on the culture surface at an initial cell density of at least $2.0 \times 10^4$ cells/cm².

* * * * *